United States Patent [19]

Kuch et al.

[11] Patent Number: 4,614,739
[45] Date of Patent: Sep. 30, 1986

[54] OXINDOLE DERIVATIVES, PHARMACEUTICAL COMPOSITIONS AND USE

[75] Inventors: Heinz Kuch, Frankfurt am Main; Hansjörg Kruse, Kelkheim, both of Fed. Rep. of Germany

[73] Assignee: Hoechst Aktiengesellschaft, Frankfurt, Fed. Rep. of Germany

[21] Appl. No.: 745,884

[22] Filed: Jun. 18, 1985

Related U.S. Application Data

[62] Division of Ser. No. 366,321, Apr. 7, 1982, Pat. No. 4,542,148.

[30] Foreign Application Priority Data

Apr. 9, 1981 [DE] Fed. Rep. of Germany ....... 3114351

[51] Int. Cl.⁴ ................ A61K 31/405; A61K 31/535; C07D 401/06; C07D 413/06
[52] U.S. Cl. .................................... 514/212; 514/234; 514/253; 514/321; 514/411; 514/414; 514/323; 544/144; 544/372; 544/373; 544/742; 546/200; 546/201; 548/431; 548/465; 540/602
[58] Field of Search ............... 544/144, 372, 373, 142; 546/200, 201; 548/431, 465; 260/245.7; 514/212, 234, 253, 321, 323, 411, 414

[56] References Cited

U.S. PATENT DOCUMENTS 4,153,789 5/1979 Kubela et al. .................... 548/465

OTHER PUBLICATIONS

Bolotov et al, *Chemical Abstracts*, vol. 84 (1976) No. 164,560t.

*Primary Examiner*—Robert W. Ramsuer
*Attorney, Agent, or Firm*—Curtis, Morris & Safford

[57] ABSTRACT

Oxindole derivatives of the general formula I

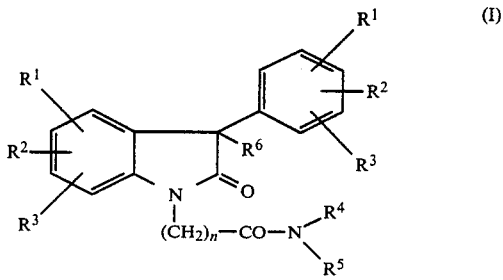

are described, and also processes for their preparation and drugs containing them. The new compounds exhibit a neuroanabolic action in various animal models.

6 Claims, No Drawings

OXINDOLE DERIVATIVES, PHARMACEUTICAL COMPOSITIONS AND USE

This application is a division of application Ser. No. 366,321, filed Apr. 7, 1982 now U.S. Pat. No. 4,542,148.

The invention relates to oxindole derivatives of the general formula I

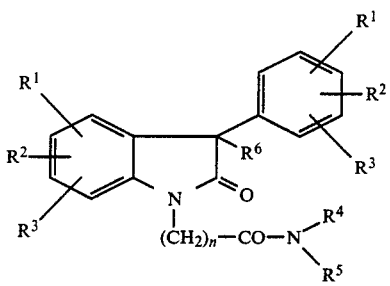

in which n denotes 1, 2 or 3, $R^1$, $R^2$ and $R^3$ are identical or different and independently of one another denote hydrogen, halogen, such as fluorine, chlorine or bromine, straight-chain or branched alkyl having 1 to 4 C atoms, trifluoromethyl, methylenedioxy, alkoxy having 1 to 3 C atoms, or nitro, $R^4$ and $R^5$ are identical or different and independently of one another denote hydrogen, straight-chain or branched alkyl which has 1 to 6 C atoms and which can be substituted by hydroxyl or alkoxy having 1 to 3 C atoms, phenylalkyl having 1 to 7 C atoms in the alkyl radical, which can also be branched, it being possible for the phenyl nucleus to be monosubstituted, disubstituted or trisubstituted by alkoxy having 1 to 3 C atoms, alkyl having 1 to 4 C atoms, methylenedioxy, halogen, such as fluorine, chlorine or bromine, or nitro, cyclopentyl, cyclohexyl, alkylcyclohexyl having 1 to 4 C atoms in the alkyl part, cycloheptyl, cyclooctyl, adamantyl, phenyl in which the phenyl nucleus can be substituted as defined above for phenylalkyl, or naphthyl or in which $R^4$ and $R^5$, together with the N atom carrying them, denote pyrrolidino, piperidino, hexahydroazepino or morpholino, each of which can be substituted by alkyl or alkoxyalkyl having 1 to 5 C atoms, N-alkylpiperazino having 1 to 5 C atoms in the alkyl part, N-phenylpiperazino which is optionally monosubstituted, disubstituted or trisubstituted by substituents in the phenyl radical as defined in the case of $R^1$, N-alkanoylpiperazino having 1 to 5 C atoms in the alkyl part, and N-benzoylpiperazino which is optionally monosubstituted, disubstituted or trisubstituted by substituents in the phenyl radical as defined in the case of $R^1$, and $R^6$ denotes hydrogen, alkyl having 1 to 5 C atoms or hydroxyl.

Preferred compounds of the formula I are those in which n denotes one, $R^1$, $R^2$ and $R^3$ are identical or different and independently of one another denote hydrogen, halogen, such as fluorine, chlorine or bromine, or straight-chain or branched alkyl having 1 to 4 C atoms, $R^4$ and $R^5$ are identical or different and independently of one another denote hydrogen, straight-chain or branched alkyl having 1 to 4 C atoms; cyclohexyl, alkylcyclohexyl having 1 to 4 C atoms in the alkyl part, cycloheptyl, cyclooctyl; phenyl which can be monosubstituted, disubstituted or trisubstituted by halogen, such as fluorine, chlorine or bromine, straight-chain or branched alkyl having 1 to 4 C atoms, trifluoromethyl, methylenedioxy or alkoxy having 1 to 3 C atoms; phenylalkyl having 1 to 3 C atoms in the alkyl part, it being possible for the phenyl nucleus to be substituted as indicated above in the case of phenyl, or hydroxyalkyl having 1 to 4 C atoms, or $R^4$ and $R^5$, together with the nitrogen atom carrying them, denote pyrrolidino, piperidino, morpholino or phenylpiperazino in which the phenyl nucleus can be substituted as described above in the case of phenyl, and $R^6$ denotes hydrogen, alkyl having 1, 2 or 3 C atoms, or hydroxyl.

Compounds of the formula I which are particularly preferred are those in which n denotes one, $R^1$ denotes hydrogen or chlorine in the 5-position of the indole; $R^2$ and $R^3$ denote hydrogen, $R^4$ and $R^5$ are identical or different and independently of one another denote hydrogen, alkyl having 1, 2 or 3 C atoms, cyclohexyl, methylcyclohexyl, cycloheptyl, cyclooctyl, hydroxyalkyl having 2 or 3 C atoms, or benzyl or phenethyl in which the phenyl radicals can in each case be monosubstituted or disubstituted in the phenyl nucleus by halogen, such as fluorine or chlorine, methylenedioxy or alkoxy having 1, 2 or 3 C atoms, or $R^4$ and $R^5$, together with the nitrogen atom carrying them, denote piperidino, pyrrolidino, morpholio or N-phenylpiperazino in which the phenyl nucleus can be monosubstituted or disubstituted by fluorine or chlorine, methylenedioxy or alkoxy having 1, 2 or 3 carbon atoms, and $R^6$ denotes hydrogen or methyl.

The compounds, according to the invention, of the formula I have an asymmetric C atom and therefore exist in stereoisomeric forms. The invention covers the racemic mixtures as well as the dextrorotary and levorotary enantiomers.

Insofar as the compounds according to the invention have a basic character, the invention also covers their salts with pharmaceutically acceptable acids, such as, for example, hydrogen halide acids, in particular hydrochloric acid, acetic acid, malic acid, tartaric acid, maleic acid, fumaric acid, methanesulfonic acid and the like.

The invention also relates to processes for the preparation of compounds of the formula I, which comprise (a) reacting carboxylic acids of the general formula II, or reactive derivatives thereof, with ammonia or primary or secondary amines of the formula XV

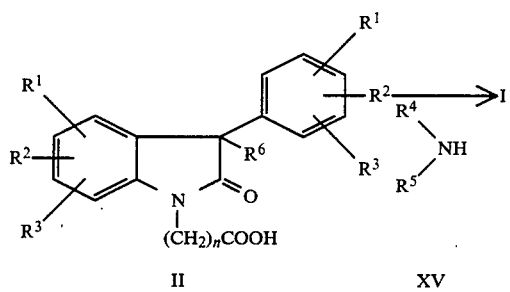

n, $R^1$, $R^2$, $R^3$ and $R^6$ in formula II having the same meaning as in formula I.

Suitable reactive derivatives of the carboxylic acids of the formula II are esters thereof with alcohols having 1-18 carbon atoms, preferably 1-5 carbon atoms, or with phenol, benzyl alcohol or phenylethyl alcohol, halides thereof, preferably chlorides and bromides, internal anhydrides if $R^6$ denotes hydrogen, mixed anhydrides with carboxylic acids having 1-6 carbon atoms, preferably carbonic acid, acetic acid or propionic acid, and the imidazolides, azides or isourea derivatives, preferably dicyclohexylisourea derivatives, of the carboxylic acids of the formula II.

(b) A further process comprises alkylating oxindole derivatives of the formula IV in which n, $R^1$, $R^2$ and $R^3$ are as defined in formula I and $R^{6'}$ denotes alkyl having 1–5 C atoms, with ω-halogenocarboxylic acid amides of the formula V in which X denotes chlorine, bromine or iodine, in the presence of a non-nucleophilic base, such as sodium hydride, sodamide, lithium amides or alkali metal alcoholates, and in an organic solvent, such as tetrahydrofuran or dimethylformamide, to give compounds of the formula I:

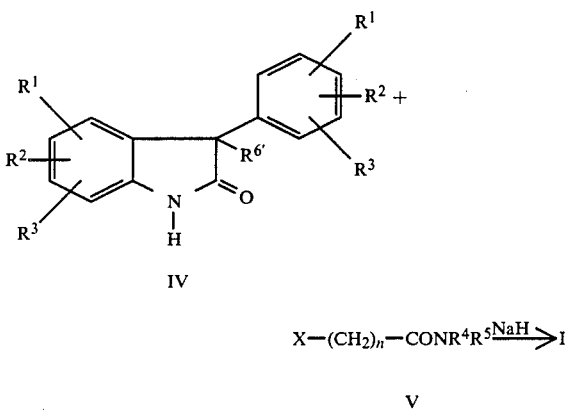

(c) A further process for the preparation of the compounds of the formula I comprises cyclizing substituted mandelic acid derivatives of the formula VI in which n, $R^1$, $R^2$, $R^3$, $R^4$ and $R^5$ have the same meaning as in formula I, $R^{6''}$ denotes hydrogen or alkyl having 1–5 carbon atoms, and $R^7$ denotes hydrogen or an acyl group having 1–6 carbon atoms, preferably acetyl, by means of acid condensation agents, such as polyphosphoric acid or concentrated sulfuric acid, at 25° to 120° C., preferably at 70° to 80° C.:

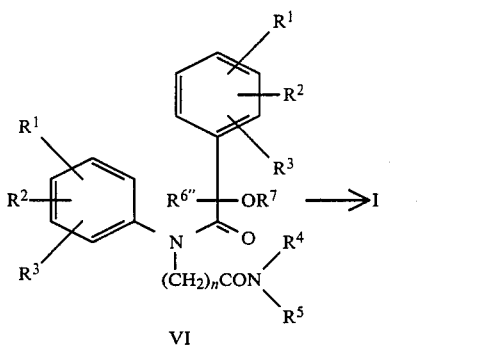

(d) A further process for the preparation of compounds of the formula I in which $R^6$ denotes hydroxyl, comprises oxidizing a compound of the formula I in which $R^6$ denotes hydrogen, in an inert organic solvent. Suitable oxidizing agents are atmospheric oxygen or peroxides.

The intermediate products, of the formula XII below and those of the formula XIV which are obtainable therefrom, for the processes (a), (c) and (d) can be obtained from substituted anilines of the formula VII in which $R^1$, $R^2$ and $R^3$ are as defined for formula I. These compounds are reacted (J. Chem. Soc. (London) 1949, 313) either with ω-halogenocarboxylic acids of the formula VIII in which Z denotes chlorine, bromine or iodine, or esters thereof IX in which $R^8$ denotes methyl, ethyl or propyl. The acids X which are obtained (Chem. Ber. 41, 3792 and 3794) in the reaction with the halogenocarboxylic acids VIII can be converted, under known conditions, for example acid catalysis, by means of alcohols XI in which $R^8$ is as defined in IX, into the corresponding esters XII; these esters XII can be obtained direct by using the halogenocarboxylic acid esters IX.

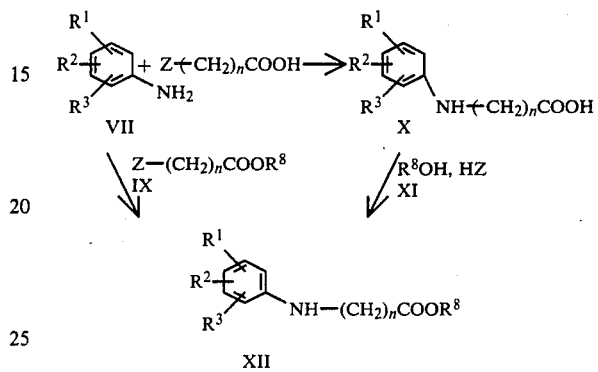

The reaction of the ω-anilinocarboxylic acid esters XII with substituted acylmandelyl chlorides of the formula XIII in which $R^1$, $R^2$ and $R^3$ are as defined in formula I, $R^{6''}$ denotes hydrogen or alkyl having 1–5 C atoms, and $R^9$ denotes alkyl having 1–4 C atoms, or phenyl, under the conditions of the Schotten-Baumann reaction (in aqueous sodium hydroxide solution) or of the Einhorn reaction (in chloroform and triethylamine), leads to the corresponding acylmandelic acid derivatives of the formula XIV:

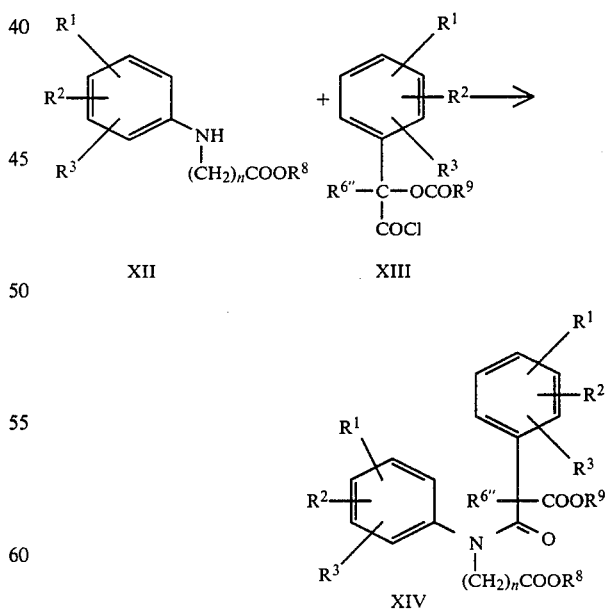

The starting materials for process (a) are prepared by cyclizing the compounds of the formula XIV by means of acid condensation agents, such as, for example, concentrated sulfuric acid or polyphosphoric acid, at 20° to 120° C., preferably at 25° to 60° C., to give the 1-oxindolylcarboxylic acid esters of the formula IIa in which Y denotes methoxy, ethoxy or propoxy:

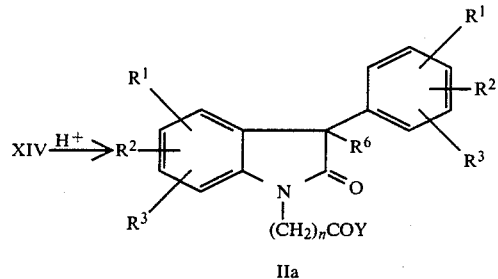

IIa

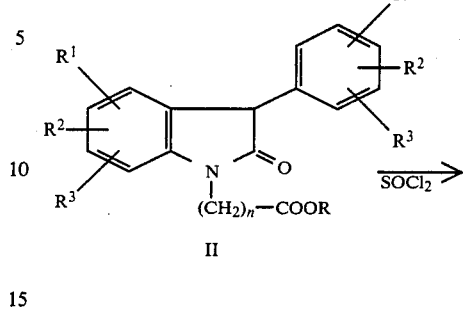

II

The process (a) is carried out by reacting the compounds of the formula IIa with the compounds of the formula XV to give the compounds, according to the invention, of the formula I. The reaction can be carried out in the absence of a solvent using an excess of amine at 25° to 150° C., preferably at 80°–100° C., or, preferably in the case of the reaction with primary amines, in a polar, protic solvent, such as methanol or ethanol.

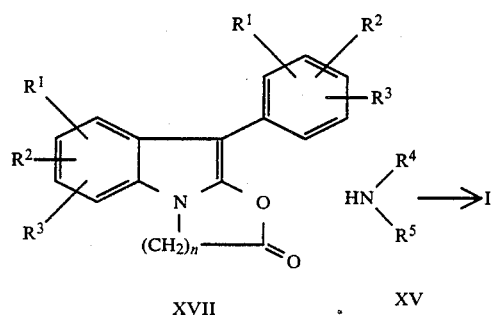

XVII . XV

The reaction with thionyl chloride or phosphorus oxychloride is carried out at −50° to +50° C., preferably at −20° to 0° C., while the subsequent reaction with a compound of the formula XV is carried out at 0° to 130° C., preferably at 20° to 50° C., in an organic solvent, preferably methylene chloride, chloroform, toluene or hexamethylphosphoric acid triamide or mixtures thereof.

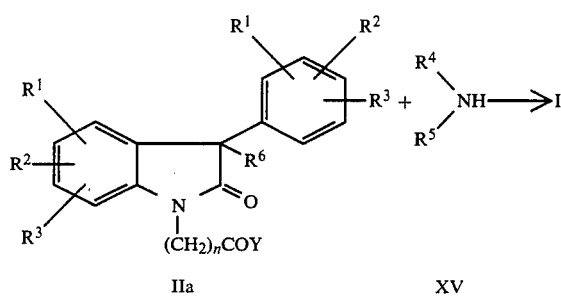

IIa         XV

The esters of the formula IIa in which Y denotes methoxy, ethoxy or propoxy, can also be hydrolyzed under alkaline conditions using sodium or potassium hydroxide solution, at room temperature to elevated temperatures, to give the corresponding salts of the carboxylic acids of the formula II. The free carboxylic acids of the formula II are obtained by adding a mineral acid, preferably hydrochloric acid. These carboxylic acids are converted into the compounds of the formula I (Angew. Chem. 74, 407 (1972)) by reaction with compounds of the formula XV in the presence of a dehydrating agent, such as carbonyldiimidazole (XVI).

Further suitable condensation agents are cyclohexylcarbodiimide, 1-hydroxybenztriazole or 1-(4-chlorobenzoyl)-2-(4-methylpiperazino)-acetylene.

The process (a) can also be carried out by converting the carboxylic acids of the formula II, by reaction with thionyl chloride or phosphorus oxychloride, into the internal anhydrides of the formula XVII, which, together with compounds of the formula XV, give the oxindole derivatives of the formula I.

The process (a) can also be carried out by converting the carboxylic acids of the formula II, by reaction with chloroformic acid esters of the formula XVIII in which $R^{10}$ denotes alkyl having 1–4 C atoms, phenyl or benzyl, into the mixed anhydrides of the formula XIX, advantageously in the presence of tertiary amines, such as triethylamine, diisopropylethylamine or dicyclohexylethylamine. The compounds of the formula XIX react with compounds of the formula XV to give the compounds, according to the invention, of the formula I:

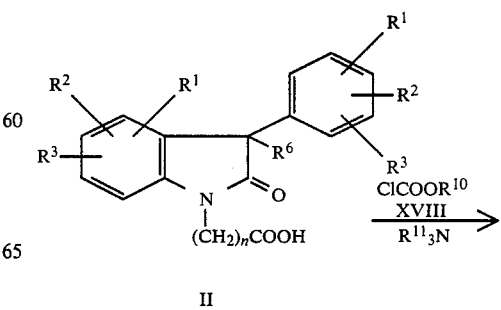

II

-continued

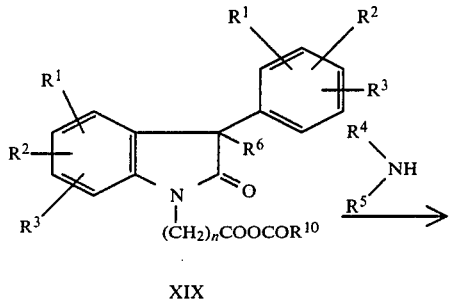

XIX

The starting materials of the formula IV for the process (b) are prepared analogously to the processes described above from the substituted anilines of the formula VII by reaction with acylmandelyl chlorides of the formula XIII and subsequent cyclization by means of acid condensation agents.

The starting compounds of the formula VI for process (c) are obtained by reacting compounds of the formula XIV with a compound of the formula XV to give the mandelic acid amide derivatives of the formula VI. This reaction is advantageously carried out in polar, protic solvents, in particular methanol or ethanol, at 25° to 80° C.:

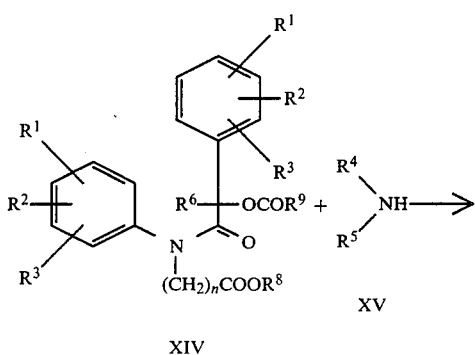

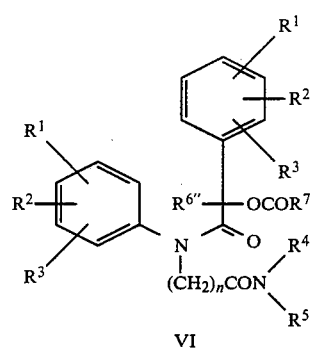

VI

The compounds of the formula I exhibit neuroanabolic properties. They affect the metabolism of the brain in an advantageous manner and can, therefore, be used for treating chronic functional disorders of the brain having a very wide variety of origins, and also acute functional disorders of the brain caused by traumatic influences. They prove to be highly active in animal models, such as have been used for characterizing the properties of substances having a neuroanabolic action (cf. German Offenlegungsschrift No. 2,701,450 and Europ. J. Pharmacol. 16, (1971) 283).

The compounds of the formula I prolong the survival time of rats under hypoxic conditions by up to over 700% when administered intraperitoneally in a dosage of 25 to 1,000 mg/kg, preferably 100 to 500 mg/kg, or when administered perorally in a dosage of 250 to 1,000 mg/kg.

The survival time of rats poisoned with nitrite is also significantly prolonged by the compounds of the formula I when administered perorally in dosages of 250 to 1,000 mg/kg.

The compounds of the formula I are distinguished by a very low toxicity. The $LD_{50}$ on mice is often above 2 g/kg of body weight, when administered intraperitoneally.

For use as drugs for peroral administration, the compounds of the formula I can be processed into tablets, dragees or capsules which, in addition to the active compounds, contain, if appropriate, customary pharmaceutical excipients, diluents and/or auxiliaries. The content of active compound is 1 to 95 percent, preferably 10 to 80 percent. Examples of suitable excipients, diluents and auxiliaries are calcium carbonate, a calcium phosphonate, sodium phosphate, lactose, corn starch, alginates, gelatine, aluminum stearate, magnesium stearate, talc or silicone oil.

A drug of this type can advantageously be formulated in dosage units which are designed to suit the desired therapy.

Drugs of this type can contain, as the active compound, 1 to 1,000 mg, advantageously 5 to 500 mg, of a compound of the formula I per individual dose.

For parenteral administration, the new active compounds are suitable in the form of injectable aqueous or oily suspensions which can, in addition, also contain suspending agents, such as, for example sodium carboxymethylcellulose, methylcellulose, hydroxypropylcellulose, sodium alginate or polyvinylpyrrolidone, dispersing agents and wetting agents, such as polyoxyethylene stearate, and preservatives; the oily suspensions can be present in groundnut oil, olive oil, coconut oil, sesame oil or paraffin oil.

EXAMPLE 1 (Process a)

(1H-2,3-Dihydro-2-oxo-3-phenyl-5-chloro-1-indolyl)-acetic acid piperidide (I, $R^1$=5-Cl, $R^2$=$R^3$=$R^6$=H, $R^4$+$R^5$=—$(CH_2)_5$—, n=1

1.1 N-(4-Chlorophenyl)-N-(2-phenyl-2-acetoxyacetyl)-glycine ethyl ester 56.2 g (0.26 mole) of N-(4-chlorophenyl)-glycine ethyl ester were dissolved in 300 ml of absolute methylene chloride. 66.6 g (0.3 mole) of acetylmandelyl chloride in 30 ml of methylene chloride were added dropwise while cooling with ice.

The mixture was then stirred for a further 24 hours at room temperature, in the course of which a white precipitate was formed. The mixture was poured into water and the organic phase was separated off and washed again with 3×500 ml of water and was dried and concentrated, and the crude oil, which still contained residual solvent, was reacted further in this state.

1.2 Ethyl (1H-2,3-dihydro-2-oxo-3-phenyl-5-chloro-1-indolyl)-acetate 109.2 g of N-(4-chlorophenyl)-N-(2-phenyl-2-acetoxyacetyl)-glycine ethyl ester were introduced into 465 ml of concentrated sulfuric acid, while cooling with ice.

After 16 hours at room temperature, the mixture was poured onto 3.5 l of ice and was then extracted with 3 l of methylene chloride. The organic phase was neutralized with 300 ml of 1N sodium bicarbonate solution, dried and concentrated. The crude product was recrystallized from isopropanol. Melting point 125° C.

1.3
(1H-2,3-Dihydro-2-oxo-3-phenyl-5-chloro-1-indolyl)acetic acid piperidide 16.5 g of ethyl (1H-2,3-dihydro-2-oxo-3-phenyl-5-chloro-1-indolyl)-acetate was dissolved in 100 ml of piperidine and heated, under nitrogen, for 24 hours on a water bath. The solution was poured into a mixture of 1.8 l of ice-water and 200 ml of glacial acetic acid. The mixture was extracted with 500 ml of ethyl acetate and the organic phase was washed with twice 600 ml of 2N acetic acid and with 4×500 ml of water and was dried and concentrated. The crude oil was recrystallized from toluene/petroleum ether; the product melted at 153° C.

EXAMPLE 2 (Process a)

(1H-2,3-Dihydro-2-oxo-3-phenyl-5-chloro-1-indolyl)-acetic acid morpholide (I, $R^1$=5-Cl, $R^2$=$R^3$=$R^6$=H,
$R^4$+$R^5$=—$(CH_2)_2O(CH_2)_2$— and n=1)

20 g of ethyl (1H-2,3-dihydro-2-oxo-3-phenyl-5-chloro-1-indolyl)-acetate were dissolved in 90 ml of morpholine and the mixture was heated, under nitrogen, on a steam bath for 5 hours. After cooling, it was poured into a mixture of 1,800 ml of ice-water, 200 ml of glacial acetic acid and 800 ml of ethyl acetate. The organic phase was separated off and washed with 2N acetic acid, saturated sodium bicarbonate solution and water and was dried and concentrated; the crude product was recrystallized from ethanol. Melting point 143°–144° C.

EXAMPLE 3 (Process a)

(1H-2,3-Dihydro-2-oxo-3-phenyl-5-chloro-1-indolyl)-N-methylacetamide (I, $R^1$=5-Cl, $R^2$=$R^3$=$R^4$=$R^6$=H, $R^5$=$CH_3$ and n=1)

A saturated solution of methylamine in toluene was added to 10 g of ethyl (1H-2,3-dihydro-2-oxo-3-phenyl-5-chloro-1-indolyl)-acetate in a pressure bottle, and the mixture was kept at room temperature for 14 hours. The solution was then concentrated to half its volume and the product which had crystallized out was filtered off and washed with toluene/petroleum ether. The crude product was recrystallized from ethanol; melting point 217°–218° C.

EXAMPLE 4 (Process a)

(2,3-Dihydro-2-oxo-3-phenyl-1-indolyl)-acetic acid N-benzylamide (I, $R^1$=$R^2$=$R^3$=$R^4$=$R^6$=H, $R^5$=$CH_2C_6H_5$ and n=1)

4.1 (2,3-Dihydro-2-oxo-3-phenyl-1-indolyl)-acetic acid 70 g (0.25 mole) of methyl (1H-2,3-dihydro-2-oxo-3-phenyl-1-indolyl)-acetate were treated with 18 g of KOH in 550 ml of 90% strength aqueous methanol for 15 hours at room temperature, the solution was then acidified (to Congo Red) with 2N HCl and the product which had been precipitated was purified by being dissolved in NaOH, clarified with active charcoal, precipitated with 2N HCl, filtered off, washed with water and dried. Melting point 180°–181° C.

4.2 (2,3-Dihydro-2-oxo-3-phenyl-1-indolyl)-acetic acid N-benzylamide 1.7 g of carbonyldiimidazole were added at room temperature to 2.7 g (10 mmoles) of the carboxylic acid in 10 ml of dry tetrahydrofuran, while stirring. After 30 minutes, 1.1 ml of benzylamine were added dropwise and after a further 15 minutes the mixture was stirred into 200 ml of water. The precipitate was filtered off, washed with water and recrystallized from ethanol. Melting point 182°–183° C.

EXAMPLE 5 (Process a)

(2,3-Dihydro-2-oxo-3-phenyl-1-indolyl)-acetic acid N-(4-trans-methylcyclohexyl)-amide (I, $R^1$=$R^2$=$R^3$=$R^4$=$R^6$=H,
$R^5$=4—$CH_3$—cyclo—$C_6H_{10}$ and n=1)

5.4 g of the carboxylic acid from Example 4.1 were reacted with 2.3 g of trans-4-methylcyclohexylamine and 3.4 g of carbonyldiimidazole analogously to the instructions in Example 4.2. Melting point 215°–216° C.

EXAMPLE 6 (Process a)

(2,3-Dihydro-2-oxo-3-phenyl-1-indolyl)-acetic acid N-benzylcyclooctylamide (I, $R^1$=$R^2$=$R^3$=$R^4$=$R^6$=H, $R^5$=cyclo—$C_8H_{15}$ and n=1)

5.4 g of the carboxylic acid from Example 4.1 were reacted with 3.4 g of carbonyldiimidazole and 2.6 g of cyclooctylamine analogously to Example 4.2. The crude product was recrystallized from ethanol. Melting point 167°–168° C.

EXAMPLE 7 (Process a)

(2,3-Dihydro-2-oxo-3-phenyl-1-indolyl)-acetic acid N-4-phenylpiperazide (I, $R^1$=$R^2$=$R^3$=$R^6$=H,
$R^4$+$R^5$=$CH_2CH_2N(C_6H_5)CH_2$—$CH_2$ and n=1)

2.7 g of the acid from Example 4.1 were reacted with 1.7 g of carbonyldiimidazole and 1.6 g of phenylpiperazine in accordance with the instructions of Example 4.2. After removing the solvent in vacuo, water was added to the residue, the mixture was extracted with toluene, the toluene extract was dried and the toluene was then removed in vacuo. The oily residue was taken up in isopropanol and slightly acidified with concentrated hydrochloric acid, and the salt precipitated was filtered off and washed with acetone. Melting point 224°–227° C.

EXAMPLE 8 (Process a)

(2,3-Dihydro-2-oxo-3-phenyl-1-indolyl)-acetic acid N-[4-(m-tolyl)-piperazide]

(I, $R^1$=$R^2$=$R^3$=$R^6$=H,
$R^4$+$R^5$=$CH_2CH_2N(m$—$CH_3C_6H_4)CH_2CH_2$ and n=1)

8.1 g of the carboxylic acid from Example 4.1 were reacted with 5.1 g of carbonyldiimidazole and 5.3 g of m-tolylpiperazine analogously to Example 7. Melting point 226°–228° C.

EXAMPLE 9 (Process a)

(2,3-Dihydro-2-oxo-3-phenyl-1-indolyl)-acetic acid N-[2-3,4-dimethoxyphenyl)-ethyl]-amide (I, $R^1 = R^2 = R^3 = R^4 = R^6 = H$, $R^5 = CH_2CH_2C_6H_3(OCH_3)$ and $n = 1$)

5.4 g of the carboxylic acid from Example 4.1 were reacted with 3.4 g of carbonyldiimidazole and 3.6 g of homoveratrylamine analogously to Example 4.2. Melting point 170°–172° C.

EXAMPLE 10 (Process a)

(2,3-Dihydro-2-oxo-3-phenyl-1-indolyl)-acetic acid N-(2-hydroxyethyl)-amide (I, $R^1 = R^2 = R^3 = R^4 = R^6 = H$, $R^5 = CH_2CH_2OH$ and $n = 1$)

5.4 g of the carboxylic acid from Example 4.1 were reacted with 3.4 g of carbonyldiimidazole and 1.2 ml of 2-aminoethanol analogously to Example 4.2. When the reaction was complete, the THF was removed in vacuo, water was added to the residue and the product was filtered off and dried. Melting point 175°–182° C.

EXAMPLE 11 (Process a)

(2,3-Dihydro-2-oxo-3-phenyl-1-indolyl)-acetic acid N-cyclohexylamide (I, $R^1 = R^2 = R^3 = R^4 = R^6 = H$, $R^5 = $cyclo—$C_6H_{11}$ and $n = 1$)

6.7 g of the carboxylic acid from Example 4.1 were dissolved in 20 ml of hexamethylphosphoric acid triamide (HMPTA) and 10 ml of methylene chloride, and 1.8 ml of thionyl chloride were added at −10° C. After stirring for 30 minutes, 2.86 ml of cyclohexylamine were added at −10° C. The solution was warmed to room temperature and stirred overnight; water was added and the product was filtered off. The crude product was purified by chromatography on silica gel using 4:1 ethyl acetate/methanol. Melting point 200°–201° C.

EXAMPLE 12 (Process a)

(2,3-Dihydro-2-oxo-3-phenyl-1-indolyl)-acetic acid N-cyclohexylamide (I, $R^1 = R^2 = R^3 = R^4 = R^6 = H$, $R^5 = $cyclo—$C_6H_{11}$ and $n = 1$)

1.3 g (5 mmoles) of the carboxylic acid from Example 4.1 were dissolved in 15 ml of absolute acetone, and 0.55 ml (5.5 mmoles) of triethylamine and 0.52 g (5.5 mmoles) of ethyl chloroformate were then added dropwise, successively, under nitrogen and while cooling with ice; after stirring for 5 minutes, 0.5 g (5 mmoles) of cyclohexylamine was added. After 30 minutes at 0° C., the mixture was warmed to room temperature, stirred for 1 hour and diluted with 30 ml of water, and the precipitate was filtered off and recrystallized from isopropanol. Melting point 205°–206° C.

EXAMPLE 13 (Process b)

(2,3-Dihydro-2-oxo-3-methyl-3-phenyl-5-chloro-1-indolyl)acetic acid N,N-diethylamide (I, $R^1 = 5$-Cl, $R^2 = R^3 = H$, $R^4 = R^5 = C_2H_5$, $R^6 = CH_3$ and $n = 1$)

13.1 3-Methyl-3-phenyl-5-chlorooxindole 10 g of 3-phenyl-5-chlorooxindole were dissolved in 100 ml of acetone and 20 ml of water, 2.9 g of potassium carbonate and 2.9 ml of methyl iodide were added and the mixture was warmed at 50° C. for 3 hours and concentrated; water was added to the residue, which was extracted with ethyl acetate, and the extract was dried over magnesium sulfate, and the solvent was removed. The residue was recrystallized from ethanol. Melting point 180°–181° C.

13.2

(2,3-Dihydro-2-oxo-3-methyl-3-phenyl-3-chloro-1-indolyl)-acetic acid N,N-diethylamide 0.4 g of sodium hydride (80% in oil) was added to a solution of 2.6 g of 3-methyl-3-phenyl-5-chlorooxindole in 25 ml of THF. After 30 minutes, 1.5 g of chloroacetic acid diethylamide in 15 ml of THF were added. After stirring for 3 hours at room temperature, the mixture was evaporated to dryness on a rotary evaporator, the residue was taken up in toluene, washed with water and dried, and the solvent was removed in vacuo. The crude product was purified by column chromatography on silica gel using 4:1 toluene/ethyl acetate, and was recrystallized from isopropanol/petroleum ether. Melting point 108°–109° C.

EXAMPLE 14 (Process c)

(2,3-Dihydro-2-oxo-3-phenyl-indolyl)-acetamide (I, $R^1 = R^2 = R^3 = R^4 = R^5 = R^6 = H$ and $n = 1$)

14.1 N-Phenyl-N-(2-phenyl-2-acetoxyacetyl)-glycine methyl ester (XIV, $R^1 = H$, $R^2 = H$, $R^5 = H$, $R^7 = CH_3$, $R^8 = CH_3$, $m = 1$ and $n = 1$)

125 g of N-phenylglycine methyl ester were dissolved in 600 ml of absolute toluene and 161 g of acetylmandeyl chloride, dissolved in 80 ml of toluene, were added dropwise (cooling with ice); a further 76.5 g of triethylamine in 200 ml of toluene were then added dropwise. After 1 hour, water was added and the organic phase was separated off, dried and concentrated.

The crude product, which still contained residual solvent, was reacted further in this state.

14.2 N-Phenyl-N-(2-phenyl-2-hydroxyacetyl)-glycine amide 15 g (44 mmoles) of N-phenyl-N-(2-phenyl-2-acetoxyacetyl)-glycine methyl ester were introduced into a solution of 25 ml of liquid ammonia in 50 ml of toluene, and the mixture was stirred at room temperature for 7 hours. The excess ammonia was expelled by warming, whereupon the product crystallized out. Melting point 148°–151° C.

14.3 (2,3-Dihydro-2-oxo-3-phenylindolyl)-acetamide 4 g (14 mmoles) of N-phenyl-N-(2-phenyl-2-hydroxyacetyl)-glycine amide were dissolved in 60 g of polyphosphoric acid, the mixture was warmed at 60° C. for 3 hours, ice was added and the mixture was extracted with ethyl acetate and the organic phase was dried and concentrated. The crude product was recrystallized from ethanol. Melting point 184°–185° C.

EXAMPLE 15 (Process a)

(2,3-Dihydro-2-oxo-3-phenyl-5-chloroindolyl)-acetamide (I, $R^1 = 5$-Cl, $R^2 = R^3 = R^4 = R^6 = H$, $R^5 = H$ and $n = 1$)

7.8 g (23.7 mmoles) of ethyl (2,3-dihydro-2-oxo-3-phenyl-5-chloro-1-indolyl)-acetate were reacted with 60 ml of liquid ammonia in 60 ml of toluene in a pressure bottle. After 15 hours at room temperature, the excess ammonia was driven off and the residue was concentrated and recrystallized from isopropanol/petroleum ether. Melting point 247°–248° C.

EXAMPLE 16 (Process a)

(2,3-Dihydro-2-oxo-3-phenyl-1-indolyl)-acetic acid morpholide (I, $R^1=R^2=R^3=R^6=H$, $R^4+R^5=CH_2CH_2OCH_2CH_2$ and $n=1$)

11 g of methyl (2,3-dihydro-2-oxo-3-phenyl-1-indolyl)-acetate were dissolved in 50 ml of morpholine and the mixture was heated under nitrogen on a steam bath for 9 hours and then poured into a mixture of glacial acetic acid and ethyl acetate; the aqueous phase was extracted with methylene chloride and the organic phase was dried and concentrated. The crude product was recrystallized from isopropanol. Melting point 153°–154° C.

EXAMPLE 17 (Process c)

(2,3-Dihydro-2-oxo-3-phenyl-1-indolyl)-acetic acid diethylamide (I, $R^1=R^2=R^3=R^6=H$, $R^4=R^5=C_2H_5$ and $n=1$)

12 g (33.5 mmoles) of N-phenyl-N-(2-phenyl-2-acetoxyacetyl)-glycine N′,N′-diethylamide, dissolved in 35 ml of toluene, were warmed with 200 g of polyphosphoric acid at 80° C. for 10 minutes, ice was then added to the mixture, which was extracted with ethyl acetate, and the organic phase was separated off and dried. After concentration, the residue was recrystallized from ethanol/petroleum ether. Melting point 144°–145° C.

EXAMPLE 18 (Process d)

(2,3-Dihydro-2-oxo-3-hydroxy-3-phenyl-1-indolyl)-N-methylacetamide (I, $R^1=R^2=R^3=R^4=H$, $R^5=CH_3$, $R^6=OH$ and $n=1$)

0.5 g (1.8 mmoles) of (2,3-dihydro-2-oxo-3-phenyl-1-indolyl)-acetamide was stirred vigorously for 20 hours in a dimethylformamide solution exposed to the air; the solution was then diluted with water, saturated with sodium chloride and extracted with ethyl acetate, and the extract was dried and concentrated. The crude product was recrystallized from ethyl acetate/petroleum ether. Melting point 183°–184° C.

EXAMPLE 19 (Process a)

2,3-Dihydro-2-oxo-3-phenylindolyl-acetamide (I, $R^{11}=R^2=R^3=R^4=R^5=R^6=H$ and $n=1$)

6.2 g of ethyl (2,3-dihydro-2-oxo-3-phenyl-1-indolyl)-acetate were reacted with 50 ml of liquid ammonia in 50 ml of toluene in a pressure bottle. After 15 hours at room temperature, the excess ammonia was removed and the residue was recrystallized from ethanol. Melting point 184°–85° C.

EXAMPLE 20 (Process c)

(1H-2,3-Dihydro-2-oxo-3-phenyl-5-chloro-1-indolyl)-acetic acid piperidide (I, $R^1=5$-Cl, $R^2=R^3=R^6=H$, $R^4+R^5=-(CH_2)-$ and $n=1$)

20.1

N-(4-chlorophenyl)-N-(2-phenyl-2-hydroxyacetyl)-glycine piperidide 25 g of N-(4-chlorophenyl)-N-(2-phenyl-2-acetoxyacetyl)-glycine ethyl ester (Example 1.1) were heated under nitrogen with 95 ml of piperidine for 18 hours on a water bath, and the mixture was then poured into a mixture of 1.5 l of ice-water and 100 ml of glacial acetic acid. The product which was precipitated was filtered off and dried and reacted further without further purification.

20.2

(1H-2,3-Dihydro-2-oxo-phenyl-5-chloro-1-indolyl)-acetic acid piperidide 13.4 g of N-(4-chlorophenyl)-N-(2-phenyl-2-hydroxyacetyl)-glycine piperidide were dissolved in 200 g of polyphosphoric acid and the mixture was warmed at 60° for 3 hours, added to ice and extracted with ethyl acetate, and the organic phase was dried and concentrated. The crude product was recrystallized from toluene/petroleum ether; the product sweats at 153° C.

EXAMPLE 21 (Process c)

(1H-2,3-Dihydro-2-oxo-3-phenyl-5-chloro-1-indolyl)-acetic acid morpholide (I, $R^1=5$-Cl, $R^2=R^3=R^6=H$, $R^4+R^5=CH_2CH_2OCH_2CH_2$ and $n=1$)

21.1

N-(4-Chlorophenyl)-N-(2-phenyl-2-hydroxyacetyl)-glycine morpholide 18.6 g of N-(4-chlorophenyl)-N-(2-phenyl-2-acetoxyacetyl)-glycine ethyl ester (Example 1.1) in 80 ml of morpholine were heated at 100° C. for 20 hours. After cooling, the product was reacted further without further purification.

21.2

(1H-2,3-Dihydro-2-oxo-3-phenyl-5-chloro-1-indolyl)-acetic acid morpholide 8 g of N-(4-chlorophenyl)-N-(2-phenyl-2-hydroxyacetyl)-glycine morpholide were introduced into 80 ml of concentrated sulfuric acid while cooling with ice. After 30 minutes the mixture was diluted with 1 l of ice-water and the product was filtered off and recrystallized from ethanol. Melting point 143°–44° C.

We claim:

1. A compound of the formula I

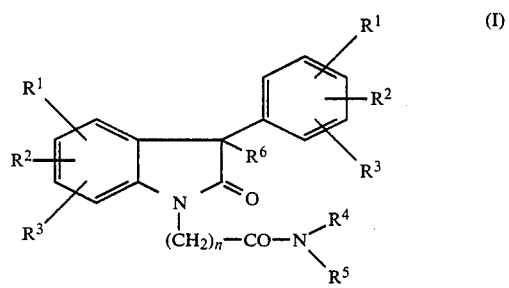

in which n is 1, 2 or 3; $R^1$, $R^2$ and $R^3$ are identical or different and independently of one another are hydrogen, halogen, straight-chain or branched alkyl having 1 to 4 C-atoms, trifluoromethyl, methylenedioxy, alkoxy having 1 to 3 C-atoms, or nitro; $R^4$ and $R^5$ together with the N-atom form a pyrrolidino, piperidino, hexahydroazepino or morpholino radical, which is unsubstituted or substituted by alkyl or alkoxyalkyl having 1 to 5 C-atoms, N-alkylpiperazino having 1 to 5 C-atoms in the alkyl radicals, N-phenylpiperazino the phenyl portion of which is unsubstituted, monosubstituted, disubstituted or trisubstituted by $R^1$, N-alkanoylpiperazino having 1 to 5 C-atoms in the alkyl portion and N-benzoylpiperazino the phenyl portion of which is unsubstituted, monosubstituted, disubstituted or trisubstituted by $R^1$; and $R^6$ is hydrogen, alkyl having 1 to 5 C-atoms or hydroxyl, or a pharmaceutically acceptable salt thereof with an acid; with the proviso that no phenyl group is substituted by trinitro or di- or tri-adjacent t-butyl.

2. The compound of claim 1 which is (1H-2,3-dihydro-2-oxo-3-phenyl-5-chloro-1-indolyl)-acetic acid piperidine or a salt thereof with a pharmaceutically acceptable acid.

3. The compound of claim 1 which is (1H-2,3-dihydro-2-oxo-3-phenyl-5-chloro-1-indolyl)-acetic acid morpholide or a salt thereof with a pharmaceutically acceptable acid.

4. The compound of claim 1 which is (1H-2,3-dihydro-2-oxo-3-phenyl-1-indolyl)-acetic acid N-4-phenylpiperazide or a salt thereof with a pharmaceutically acceptable acid.

5. A neuroanabolic composition comprising an effective amount of a compound as defined in claim 1 and an acceptable pharmaceutical excipient, diluent or auxiliary therefor.

6. A method of treating a patient having a functional disorder of the brain which comprises administering to the patient an effective amount of a compound as defined in claim 1.

* * * * *